United States Patent
Sung et al.

(10) Patent No.: US 10,359,422 B2
(45) Date of Patent: Jul. 23, 2019

(54) BIOCHIP AND METHOD FOR MANUFACTURING BIOCHIP

(71) Applicant: SCHOLAR FOXTROT CO., LTD., Mapo-gu, Seoul (KR)

(72) Inventors: Hyuk-Kee Sung, Seoul (KR); Jong Seong Kim, Seoul (KR)

(73) Assignee: SCHOLAR FOXTROT CO., LTD., Seoul (KR)

( * ) Notice: Subject to any disclaimer, the term of this patent is extended or adjusted under 35 U.S.C. 154(b) by 0 days.

(21) Appl. No.: 15/568,634

(22) PCT Filed: Dec. 23, 2016

(86) PCT No.: PCT/KR2016/015172
§ 371 (c)(1),
(2) Date: Oct. 23, 2017

(87) PCT Pub. No.: WO2017/116078
PCT Pub. Date: Jul. 6, 2017

(65) Prior Publication Data
US 2018/0149641 A1    May 31, 2018

(30) Foreign Application Priority Data

Dec. 29, 2015  (KR) .................. 10-2015-0188729
Mar. 30, 2016  (KR) .................. 10-2016-0038665
(Continued)

(51) Int. Cl.
*G01N 33/544*      (2006.01)
*C12Q 1/68*        (2018.01)
(Continued)

(52) U.S. Cl.
CPC ............. *G01N 33/544* (2013.01); *C12Q 1/68* (2013.01); *G01J 1/46* (2013.01); *G01N 21/41* (2013.01);
(Continued)

(58) Field of Classification Search
CPC ...... C08L 33/26; C08L 2205/02; C08L 39/06; B01J 2219/00596; B01J 20/267;
(Continued)

(56) References Cited

U.S. PATENT DOCUMENTS 4,912,032 A * 3/1990 Hoffman ............. A61K 9/2027
435/7.1
8,840,839 B2    9/2014 Iordanov et al.
(Continued)

FOREIGN PATENT DOCUMENTS

| CN | 100393760 | 6/2008 |
|---|---|---|
| KR | 10-2002-0026275 | 4/2002 |
| KR | 10-2003-0031895 | 4/2003 |

OTHER PUBLICATIONS

International Search Report, International Patent Application No. PCT/KR2016/015172, dated Mar. 29, 2017.
(Continued)

*Primary Examiner* — Betty J Forman
(74) *Attorney, Agent, or Firm* — Casimir Jones, SC; Robert A. Goetz

(57) ABSTRACT

Disclosed are a biochip capable of detecting and analyzing multivalent bindings between target protein and binding mediator from monovalent bindings and a method for manufacturing the same. A biochip according to an embodiment comprises: a hydrogel functional layer on which a binding mediator is formed and of which physical properties are changed by a reaction between target protein to be introduced and the binding mediator; and a transducer configured
(Continued)

to deliver a displacement signal corresponding to a change in the physical properties of the hydrogel functional layer to an analysis instrument, wherein the reaction is multivalent bindings between the target protein and the binding mediator, and de-swelling occurs in at least a portion of the hydrogel functional layer by the multivalent bindings.

8 Claims, 11 Drawing Sheets

(30) Foreign Application Priority Data

Jun. 28, 2016 (KR) .................. 10-2016-0081008
Nov. 10, 2016 (KR) .................. 10-2016-0149507

(51) Int. Cl.
| | |
|---|---|
| *G01J 1/46* | (2006.01) |
| *G01N 21/41* | (2006.01) |
| *G01N 21/77* | (2006.01) |
| *G01N 33/68* | (2006.01) |
| *G01N 33/543* | (2006.01) |
| *G01N 33/545* | (2006.01) |
| *G01N 21/552* | (2014.01) |
| *C08L 33/26* | (2006.01) |

(52) U.S. Cl.
CPC ............ *G01N 21/553* (2013.01); *G01N 21/77* (2013.01); *G01N 21/7703* (2013.01); *G01N 33/545* (2013.01); *G01N 33/54373* (2013.01); *G01N 33/68* (2013.01); *C08L 33/26* (2013.01); *G01N 2021/7723* (2013.01); *G01N 2021/7776* (2013.01); *G01N 2021/7789* (2013.01)

(58) Field of Classification Search
CPC ........... B01J 2219/00644; C12N 15/70; C12N 15/52; C12N 15/62; C12N 9/0006; C12N 9/0008; C12N 9/0016; C12N 9/93; C12N 9/001; C12N 9/1029; C12N 9/96; C08G 63/64; C08G 63/676; C08G 63/00; C08G 65/329; C12Y 604/01002; C12Y 103/01; C12Y 203/01041; C12Y 101/01059; C12Y 102/01075; C12Y 304/21004; C12Y 304/21073; G01N 33/68; G01N 15/1434; G01N 29/022; G01N 29/2462

See application file for complete search history.

(56) References Cited

U.S. PATENT DOCUMENTS

| | | | |
|---|---|---|---|
| 2006/0024813 A1* | 2/2006 | Warthoe | B82Y 15/00 435/287.1 |
| 2010/0042042 A1* | 2/2010 | Iordanov | A61B 5/0031 604/66 |
| 2014/0363901 A1* | 12/2014 | Fattinger | G01N 21/552 436/501 |

OTHER PUBLICATIONS

Ahmed, E.M., "Hydrogel: Preparation, Characterization, and Applications: A Review", Journal of Advanced Research, 2013 (Published online), vol. 6, pp. 105-121. see p. 115.

Krsko, P. et al. "Biointeractive Hydrogels", Materials Today, 2005, vol. 8, No. 12, pp. 36-44.

Bilgic, T. et al. "Surface-initiated Controlled Radical Polymerization Enhanced DNA Biosensing", European Polymer Journal, 2014 (Published online), vol. 62, pp. 281-293, see p. 286.

\* cited by examiner

Carbodiimide crosslingking

BIOCHIP AND METHOD FOR MANUFACTURING BIOCHIP

TECHNICAL FIELD

The following description relates to a biochip for detecting and analyzing multivalent bindings of target protein distinguishably from monovalent bindings, and method of manufacturing the biochip.

BACKGROUND ART

Proteins play significant roles in a human body as a regulatory factor that mediates physiological functions. Mechanism by which proteins interact with biological molecules including proteins, DNA, and/or RNA is pivotal to understand their functions that are regulated by multivalent bindings between heterologous or homologous proteins. Multivalent bindings of protein in a body may perform the following functions of:

(1) generating (e.g., thrombogenesis and actin polymerization) a structure by a protein polymerization, (2) transmitting signals inside a cell by forming a dimer or multimer through binding of a ligand (glyco)protein to a (glyco)protein between heterologous or homologous membrane proteins, and (3) expressing a gene through an interaction and binding between intracellular proteins.

As described above, a significant biomodulation, such as thrombus formation in vivo, cancerization and an immune reaction, may occur due to multivalent bindings between proteins in vivo. Accordingly, the multivalent bindings between the proteins in human body need to be detected and analyzed. To detect multivalent bindings of the proteins, a pretreatment process, such as fluorescent labeling, is required in addition to purification of proteins. When such a series of pretreatment processes is not performed, i.e., label-free, it is very difficult to detect multivalent bindings between target protein and binding mediator distinguishably from monovalent bindings. For example, even when a refractive index transducer technology according to conventional arts is used, it is difficult for the refractive index transducer to provide sensitivity enough to detect multivalent bindings and to selectively distinguish multivalent bindings from monovalent bindings.

DISCLOSURE OF THE INVENTION

Technical Problem

A biochip for detecting multivalent bindings between target protein and binding mediator distinguishably from monovalent bindings, and a method of manufacturing the biochip are provided.

However, the problems to be solved are not limited to the foregoing problems, and other problems not mentioned herein would be clearly understood by a person skilled in the art from the following description.

Technical Solutions

According to an aspect, there is provided a biochip including a hydrogel functional layer on which a binding mediator is formed and of which physical properties are changed by a reaction between target protein to be introduced and the binding mediator; and a transducer configured to deliver a displacement signal corresponding to a change in the physical properties of the hydrogel functional layer to an analysis instrument, wherein the reaction is multivalent bindings between the target protein and the binding mediator, and de-swelling occurs in at least a portion of the hydrogel functional layer by the multivalent bindings.

The physical properties may include a refractive index of at least a portion of the hydrogel functional layer, the transducer may include a waveguide, and the displacement signal may be an output signal of the waveguide.

The physical properties may include a refractive index of at least a portion of the hydrogel functional layer, the transducer may include a gold thin film, and the displacement signal may be an output signal corresponding to a surface plasmon resonance (SPR) occurring in the gold thin film.

The hydrogel functional layer may include a copolymer formed of main monomer and comonomers. The main monomer may be one of N-isopropylacrylamide, poly(N-acryloylglycinamide), hydroxypropylcellulose, poly(vinylcaprolactame) and polyvinyl methyl ether. The comonomers may be at least one of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

The hydrogel functional layer may further include a crosslinking agent. The hydrogel functional layer may include 55 to 98% of the main monomer, 2 to 40% of the comonomers and 0.1 to 5% of the crosslinking agent.

The hydrogel functional layer may include at least one of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

The binding mediator may be at least one of a ligand, a receptor, deoxyribonucleic acid (DNA) and ribonucleic acid (RNA), and a surface of the hydrogel functional layer may be modified by forming the binding mediator.

The binding mediator may be at least one of a ligand, a receptor, DNA and RNA, and a surface of the hydrogel functional layer may be modified using at least one of nanoparticle and protein as a coupling moiety to form the binding mediator.

The ligand or the receptor may be linked to the hydrogel functional layer by at least one of carbodiimide crosslinking, Schiff base crosslinking, azlactone crosslinking, carbonyldiimidazole (CDI) crosslinking, iodoacetyl crosslinking, hydrazide crosslinking, Mannich crosslinking and maleimide crosslinking.

The hydrogel functional layer may be divided into at least two regions for reaction with the target protein.

According to another aspect, there is provided a method of manufacturing the hydrogel functional layer in the above-described biochip, the method including mixing 55 to 98% of main monomer, 2 to 40% of comonomers and 0.1 to 5% of a crosslinking agent so that a sum of the main monomer and the comonomers is 100%; heating an aqueous solution containing the main monomer and the comonomers; initiating a reaction by adding an initiator; and acquiring an aqueous hydrogel solution generated by the reaction.

The acquiring of the aqueous hydrogel solution may include maintaining an oxygen-free environment while heating the aqueous solution.

The main monomer may be one of N-isopropylacrylamide, poly(N-acryloylglycinamide), hydroxypropylcellulose, poly(vinylcaprolactame) and polyvinyl methyl ether. The comonomers may be at least one of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

According to another aspect, there is provided a method of manufacturing the above-described biochip, the method including synthesizing hydrogel in a form of nanoparticles; activating a surface of the transducer with at least one of positive charge, negative charge, epoxy and mercapto; and forming the hydrogel functional layer by applying the hydrogel to the surface of the transducer.

The synthesizing of the hydrogel may include mixing 55 to 98% of main monomer, 2 to 40% of comonomers and 0.1 to 5% of a crosslinking agent so that a sum of the main monomer and the comonomers is 100%; heating an aqueous solution containing the main monomer and the comonomers; initiating a reaction by adding an initiator; and acquiring an aqueous hydrogel solution generated by the reaction. The main monomer may be one of N-isopropylacrylamide, poly(N-acryloylglycinamide), hydroxypropylcellulose, poly(vinylcaprolactame) and polyvinyl methyl ether. The comonomers may be at least one of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

The hydrogel functional layer may include at least one of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

The activating of the surface of the transducer with at least one of the positive charge, the negative charge, the epoxy and the mercapto may include activating the surface of the transducer using at least one of aminosilane, carboxylsilane, epoxysilane and mercaptosilane.

The method may further include modifying a surface of the hydrogel functional layer by forming at least one of a ligand, a receptor, DNA and RNA on the surface of the hydrogel functional layer.

The method may further include modifying a surface of the hydrogel functional layer using at least one of nanoparticles and protein as a coupling moiety to form at least one of a ligand, a receptor, DNA and RNA on the surface of the hydrogel functional layer.

The modifying of the surface may include linking at least one of the ligand, the receptor, the DNA and the RNA to the surface of the hydrogel functional layer, using at least one crosslinking agent among 1-ethyl-3-(3-dimethylaminopropyl)carbodiimide (EDC) hydrochloride, dicyclohexylcarbodiimide (DCC), sodium cyanoborohydride (NaCNBH3), azlactone, carbonyldiimidazole (CDI), iodoacetyl, hydrazide, diaminodipropylamine (DADPA) and N-hydroxysuccinimide (NHS) esters.

According to another aspect, there is provided a method of manufacturing the above-described biochip, the method including activating a surface of the transducer with at least one of positive charge, negative charge, epoxy and mercapto; applying an aqueous hydrogel solution to the surface of the transducer; and forming the hydrogel functional layer in a form of a bulk gel by adding an initiator to the aqueous hydrogel solution.

The aqueous hydrogel solution may include 55 to 98% of a main monomer, 2 to 40% of comonomers and 0.1 to 5% of a crosslinking agent.

The hydrogel functional layer may include at least one of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

The method may further include modifying a surface of the hydrogel functional layer by forming at least one of a ligand, a receptor, DNA and RNA on the surface of the hydrogel functional layer.

The method may further include modifying a surface of the hydrogel functional layer using at least one of nanoparticles and a protein as a coupling moiety to form at least one of a ligand, a receptor, DNA and RNA on the surface of the hydrogel functional layer.

Effect of the Invention

According to example embodiments, a biochip may detect multivalent bindings between target protein and binding mediator distinguishably from monovalent bindings without a pretreatment process, such as fluorescent labeling.

BEST MODE FOR CARRYING OUT THE INVENTION

Figure 1:
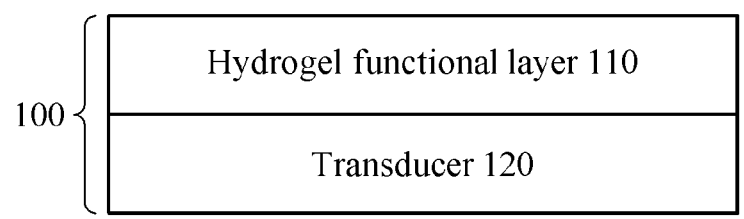
FIG. 1 is a diagram illustrating a structure of a biochip according to an example embodiment.

Hereinafter, example embodiments will be described in detail below with reference to the accompanying drawings, and like reference numerals refer to the like elements throughout.

Various modifications may be made to the example embodiments. However, it should be understood that these embodiments are not construed as limited to the illustrated forms and include all changes, equivalents or alternatives within the idea and the technical scope of this disclosure.

The terminology used herein is for the purpose of describing particular example embodiments only and is not intended to be limiting. As used herein, the singular forms "a," "an" and "the" are intended to include the plural forms as well, unless the context clearly indicates otherwise. It will be further understood that the terms "include" and/or "have," when used in this specification, specify the presence of stated features, integers, steps, operations, elements, components or combinations thereof, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which these example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Regarding the reference numerals assigned to the elements in the drawings, it should be noted that the same elements will be designated by the same reference numerals, wherever possible, even though they are shown in different drawings. Also, in description of example embodiments, detailed description of well-known related structures or functions will be omitted when it is deemed that such description will cause ambiguous interpretation of the present disclosure.

<Summary of Biochip>

FIG. 1 illustrates a structure of a biochip according to an example embodiment.

Referring to FIG. 1, the biochip according to an example embodiment includes a hydrogel functional layer 110 on which binding mediator is formed and of which physical properties are changed by a reaction between target protein to be introduced and the binding mediator, and a transducer 120 that is configured to transmit displacement signal corresponding to a change in the physical properties of the hydrogel functional layer to an analysis instrument.

The physical properties may collectively refer to mechanical properties, such as a strength, a hardness, an elongation, and the like, electromagnetic properties, such as an electrical conductivity, a resistivity, a permeability, a refractive index, and the like, thermal properties, such as a thermal conductivity, a coefficient of thermal expansion, a specific heat, and the like, and temperature properties, such as a melting point, a boiling point, and the like.

A biochip 100 may be mounted in an analysis instrument (not shown in drawings), for example, a biosensor, and the like, and may further include a physical interface (wired or wireless) to transmit displacement signal to the analysis instrument.

The analysis instrument may be an equipment to visually/acoustically/tactually provide a user with an analysis result associated with multivalent bindings between the target protein and the binding mediator. The analysis instrument may be, for example, Reichert®'s surface plasmon resonance (SPR) equipment. Depending on implementation, the analysis instrument may be a mobile device. The biochip 100 may be designed to be detachable from various analysis instruments and may be replaceable.

The hydrogel functional layer 110 may provide a resolution capability to distinguish multivalent bindings between target protein introduced to the biochip 100 and a binding mediator from monovalent bindings. When the hydrogel functional layer 110 is used, multivalent bindings between the target protein and the binding mediator may be distinguished from monovalent bindings, without labeling of a fluorescent molecule (label-free).

The binding mediator may be formed on a surface of the hydrogel functional layer 110 for a reaction with the target protein. The binding mediator may include, for example, at least one of a receptor, a ligand, deoxyribonucleic acid (DNA) and ribonucleic acid (RNA). For example, the binding mediator may be implemented by mixing at least two of the receptor, the ligand, the DNA and the RNA. The binding mediator formed on the hydrogel functional layer 110 may be specifically designed to make multivalent bindings with a specific target protein.

The multivalent bindings (or a dimerization or oligomerization) between the target protein and the binding mediator may cause de-swelling to occur in at least a portion of the hydrogel functional layer 110. Due to the de-swelling, the physical properties of the hydrogel functional layer 110 may change. On the other hand, the de-swelling of the hydrogel functional layer 110 is negligible under monovalent binding circumstance. Consequently, the monovalent bindings and the multivalent bindings between the target protein and the binding mediator may be distinguished from each other using the hydrogel functional layer 110.

In an example, the physical properties of the hydrogel functional layer 110 may include a refractive index.

In another example, the physical properties of the hydrogel functional layer 110 may include a volume of the hydrogel functional layer 110.

The transducer 120 may deliver a displacement signal, which corresponds to a change in the physical properties of the hydrogel functional layer 110 due to the multivalent bindings between the target protein introduced to the biochip 100 and the binding mediator to an analysis instrument. In an example, the transducer 120 may further include a physical interface (not shown) configured to deliver the displacement signal to an external analysis instrument. In another example, the transducer 120 may further include a signal processor (not shown) configured to process the displacement signal, and a physical interface configured to transmit a result of the processing to an external device. It is obvious to one of ordinary skilled in the art that a structure and function of the transducer 120 may be properly changed depending on application examples of the biochip 100 described in the present specification.

In an example, when a refractive index of the hydrogel functional layer 110 is changed due to de-swelling occurring in at least a portion of the hydrogel functional layer 110, the transducer 120 may be a waveguide to deliver displacement signal that is either optical signal or electrical one corresponding to a change in the refractive index due to multivalent bindings between the target protein and the binding mediator to the analysis instrument. The waveguide may be, for example, one of an SPR waveguide, a ring resonator waveguide, a long-period fiber grating waveguide, a grating coupler and a grated waveguide.

In another example, when a volume of the hydrogel functional layer 110 is changed due to de-swelling occurring in at least a portion of the hydrogel functional layer 110, the transducer 120 may include a piezoelectric element configured to deliver the displacement signal corresponding to a change in the volume due to multivalent bindings between the target protein and the binding mediator to the analysis instrument. In this example, a quartz crystal microbalance (QCM) may be used as the analysis instrument.

Depending on a number of multivalent bindings between the target protein and the binding mediator or a degree by which the multivalent bindings are concentrated, the physical properties of the hydrogel functional layer 110 may change. Based on the above relationship, using a lookup table (not shown) generated by comparing an amount of multivalent bindings and change values in the physical properties of the hydrogel functional layer 110, multivalent bindings between the target protein and the binding mediator may be detected and an amount of the multivalent bindings may be evaluated. The lookup table may be recorded in a memory connected to an external analysis instrument, such as a biosensor, connected to the biochip 100 via a physical interface.

Figure 2:
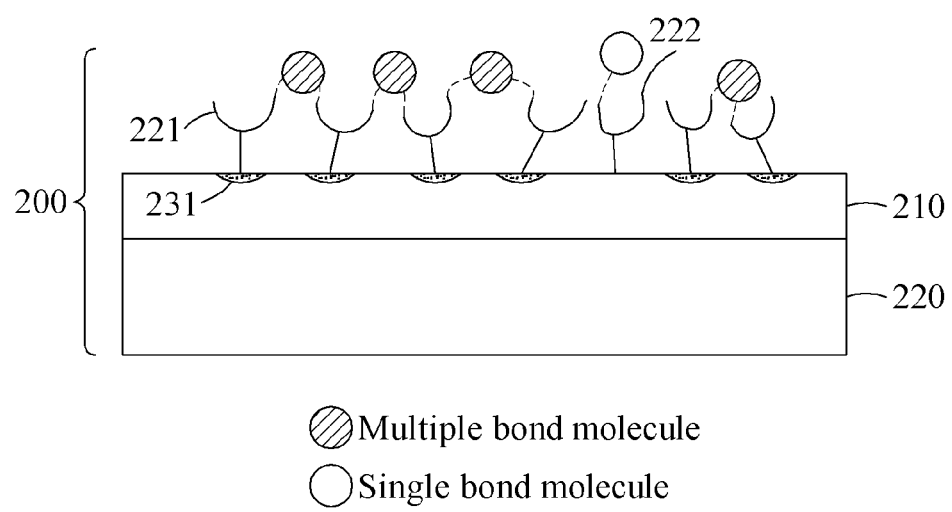
FIG. 2 is a diagram illustrating an operating principle of a biochip according to an example embodiment.

FIG. 2 illustrates an example in which a target protein reacts with a biochip 200 including a hydrogel functional layer 210 and a transducer 220 according to an example embodiment.

Referring to FIG. 2, when target proteins are bound to binding mediators formed on the hydrogel functional layer 210, multivalent bindings (dimerization) 221 or monovalent bindings 222 between the target protein and the binding mediators 211 and 222 may occur based on a type of the target protein. When multivalent bindings occur, de-swelling may accordingly occur in a region 231 of the hydrogel functional layer 210 in which the multivalent bindings occur, which may change physical properties of the hydrogel functional layer 210. In a region in which monovalent bindings occur, the physical properties of the hydrogel functional layer 210 may rarely change.

In an example, the physical properties may include a refractive index of the hydrogel functional layer 210, and the transducer 220 may transmit displacement signal corresponding to a change in the refractive index due to the region 231 of the hydrogel functional layer 210 to an analysis instrument. In this example, the transducer 220 may be a waveguide. Due to the change in the refractive index caused by the region 231, an effective refractive index of the waveguide that is the transducer 220 may change. A resonant frequency of optical signal input to the biochip 200 through a light source of an analysis instrument (not shown) may be shifted due to a change in the effective refractive index in the transducer 220, and the optical signal with the shifted resonant frequency or electrical signal (that is, the displacement signal) corresponding to the optical signal with the shifted resonant frequency may be transmitted to either optical or electrical detector of the analysis instrument. The analysis instrument may analyze the displacement signal and may measure an amount of multivalent bindings between the target protein and the binding mediator.

In another example, the physical properties may include a refractive index of the hydrogel functional layer 210, and the transducer 220 may transmit displacement signal corresponding to a change in the refractive index due to the region 231 of the hydrogel functional layer 210 to an analysis instrument. In this example, the transducer 220 may be a combination of a gold thin film and a glass. Due to the change in the refractive index caused by the region 231, an SPR may occur in the gold thin film that is the transducer 220. A path of signal input to the biochip 200 through an analysis instrument (not shown) may change due to the SPR occurring in the gold thin film, or leakage signal may be generated on the gold thin film. The displacement signal (that is, output optical signal or electrical one corresponding to the optical signal), such as the signal corresponding to the path change or the amount of the leakage signal, may be delivered to a detector of the analysis instrument.

In still another example, the physical properties may include a volume, and the transducer 220 may include a piezoelectric element configured to transmit an electrical signal (that is, a displacement signal) corresponding to a change in a volume of the region 231 of the hydrogel functional layer 110 to an analysis instrument. The analysis instrument may analyze the displacement signal and may measure an amount of multivalent bindings between the target protein and the binding mediator corresponding to the change in the volume of the region 231.

<Summary of Mechanism of Hydrogel Functional Layer>

Figure 3A:
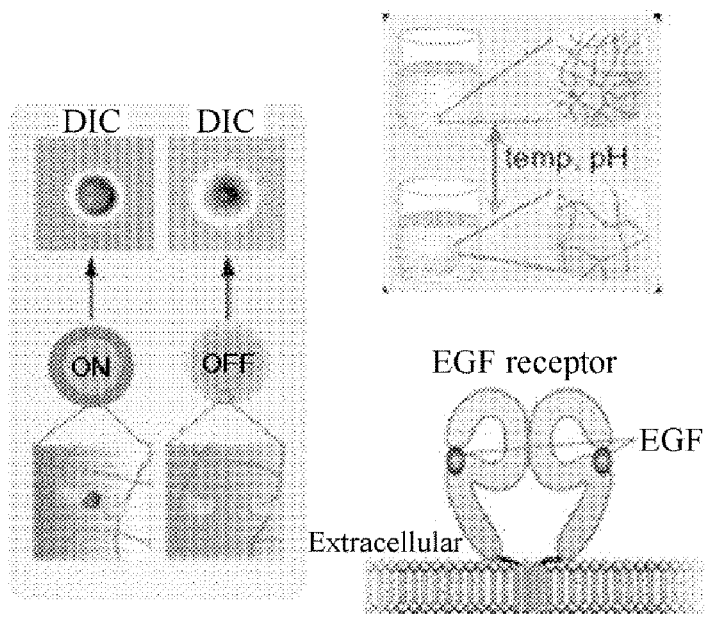
FIG. 3A illustrates an example of a differential interference contrast (DIC) microscopy image to characterize and compare changes in a refractive index of hydrogel functional layer due to monovalent bindings and multivalent bindings of target protein, and changes in a temperature and pH according to an example embodiment.
Figure 3B:
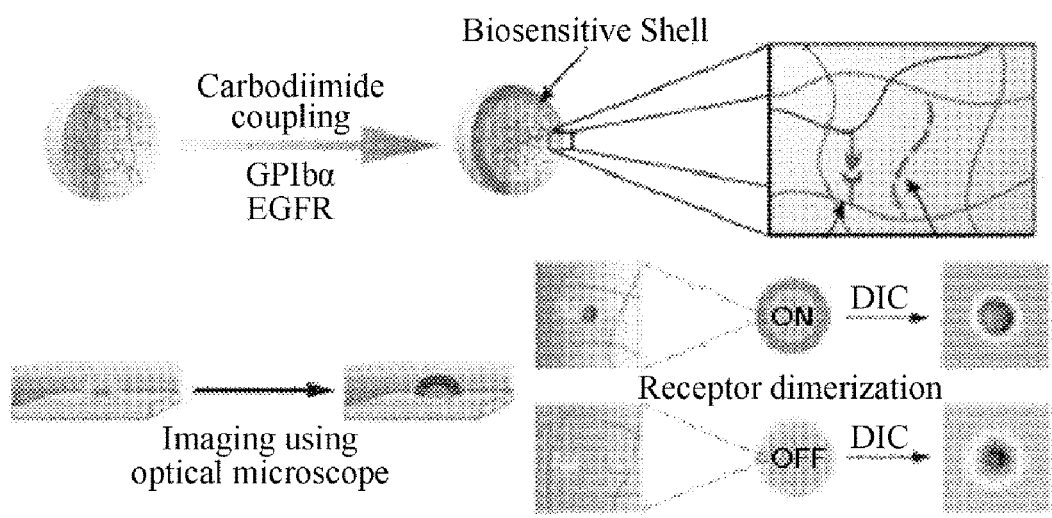
FIG. 3B illustrates an example of hydrogel functional layer of which a surface is modified by carbodiimide crosslinking between target protein and a ligand or a receptor, and an analysis of multivalent bindings using an optical microscope according to an example embodiment.

FIGS. 3A and 3B illustrate a change in physical properties (e.g., a refractive index) of a hydrogel functional layer due to monovalent and multivalent bindings, using a change in an optical microscope image according to an example embodiment.

Referring to FIGS. 3A and 3B, the physical properties (e.g., a refractive index) of the hydrogel functional layer are changed due to multivalent bindings between target protein and binding mediator occurred on the hydrogel functional layer. For example, when multivalent bindings between the target protein and the binding mediator on the hydrogel functional layer occur, de-swelling may accordingly occur in at least a portion of the hydrogel functional layer due to dimerization or multimerization. As described above, the binding mediator may include, for example, at least one of a receptor, a ligand, DNA and RNA. For example, the binding mediator may be implemented by mixing at least two of the receptor, the ligand, the DNA and the RNA. Binding mediators may be variously combined and designed to detect multivalent bindings between the target protein and the binding mediator.

A biochip described in the present disclosure may effectively detect multivalent bindings between target protein and binding mediator using a hydrogel functional layer. For example, if the bindings between the target protein and the binding mediator are not multivalent ones, physical properties of the hydrogel functional layer may rarely change. If multivalent bindings occur between the target protein and the binding mediator, the physical properties of the hydrogel functional layer may significantly change due to de-swelling of the hydrogel functional layer. Thus, it is possible to distinguish monovalent bindings from multivalent bindings between the target protein and the binding mediator using the hydrogel functional layer, and also possible to easily detect an amount of the multivalent bindings between the target protein and the binding mediator based on a change in the physical properties of the hydrogel functional layer.

Some of the physical properties of the hydrogel functional layer may change based on a reactant or a method of preparing a hydrogel functional layer.

According to an example embodiment, a hydrogel functional layer may be prepared by a multi-channel scheme. In an example, a physical region of the hydrogel functional layer may be divided into at least two regions so that a single biochip may detect various types of multivalent bindings between different pairs of target proteins and binding mediators. In another example, transducers may be included for each of channels of a hydrogel functional layer, and alternatively a single transducer may deliver a change in physical properties of the hydrogel functional layer corresponding to at least two channels. This will be further described with reference to FIG. 7 below.

The hydrogel functional layer may include a copolymer formed of a main monomer and comonomers. For example, the hydrogel functional layer may be formed by polymerizing a main monomer and comonomers using a crosslinking agent. Desirably, monomers capable of forming a hydrogel that is sensitive to heat, an ionic strength or pH may be used.

For example, the main monomer may be one of N-isopropylacrylamide, poly(N-acryloylglycinamide), hydroxypropylcellulose, poly(vinylcaprolactame) and polyvinyl methyl ether. The comonomers may be one of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

The hydrogel functional layer may include 55 to 98% of the main monomer, 2 to 40% of the comonomers and 0.1 to 5% of a crosslinking agent. When the amount of the main monomer is less than 55%, a reactivity may decrease. When the amount of the main monomer exceeds 98%, a capability to detect multivalent bindings may decrease. When the amount of the comonomers is less than 2% or exceeds 40%, a capability to detect multivalent bindings may decrease. When the amount of the crosslinking agent is less than 0.1%, it may be difficult to form the hydrogel functional layer. When the amount of the crosslinking agent exceeds 5%, a capability to detect multivalent bindings may decrease.

The hydrogel functional layer may include at least one of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

For example, desirably, the main monomer may be N-isopropylacrylamide (a temperature-sensitive hydrogel), and the comonomer may be acrylic acid (a pH-sensitive hydrogel). In this example, a crosslinking agent may be N, N'-methylene-bis-acrylamide (BIS).

The hydrogel functional layer may further include an initiator as a factor to initiate a polymerization reaction. The initiator may include, for example, ammonium persulfate (APS).

For example, the hydrogel functional layer may include 55 to 98% of N-isopropylacrylamide, 2 to 40% of acrylic acid, and 0.1 to 5% of a BIS crosslinking agent.

In particular, when acrylic acid is used as the comonomer, at least 2% of the acrylic acid may desirably be included in materials that form the hydrogel functional layer.

According to an example embodiment, a hydrogel functional layer may control a sensitivity to multivalent bindings by adjusting a ratio between components, and thus there is no limitation to examples described in the present disclosure. For example, when a specific gravity of acrylic acid increases and a specific gravity of a BIS crosslinking agent decreases, a reactivity (e.g., a degree of de-swelling) of the hydrogel functional layer to multivalent bindings between target protein and binding mediator may increase.

A surface of a transducer in a biochip according to an example embodiment may be modified to increase a bonding strength to the hydrogel functional layer.

The physical properties of the hydrogel functional layer may change in the entire hydrogel functional layer or a portion of the surface of the hydrogel functional layer.

A portion of the hydrogel functional layer in which a refractive index is changed due to multivalent bindings may be referred to as an "activated layer." The thickness of the activated layer may be equal to or smaller than that of the hydrogel functional layer. The activated layer may be formed over a predetermined depth from the surface of the hydrogel functional layer.

In an example, the surface of the hydrogel functional layer may be modified by forming a binding mediator. In another example, the surface of the hydrogel functional layer may be modified using at least one of nanoparticles and protein as a coupling moiety to form a binding mediator.

As described above, the binding mediator may include, for example, at least one of a receptor, a ligand, DNA and RNA. For example, the binding mediator may be implemented by mixing at least two of the receptor, the ligand, the DNA and the RNA. The binding mediator formed on the hydrogel functional layer 110 may be specifically designed to detect multivalent bindings.

The binding mediator may be formed on the hydrogel functional layer by carbodiimide crosslinking, Schiff base crosslinking, azlactone crosslinking, carbonyldiimidazole (CDI) crosslinking, iodoacetyl crosslinking, hydrazide crosslinking, Mannich crosslinking or maleimide crosslinking. A carboxylic acid functional group (COOH) present on the surface of the hydrogel functional layer, and a $NH_2^+$ group present on a protein may be used to form the binding mediator on the surface of the hydrogel functional layer.

Figure 4:
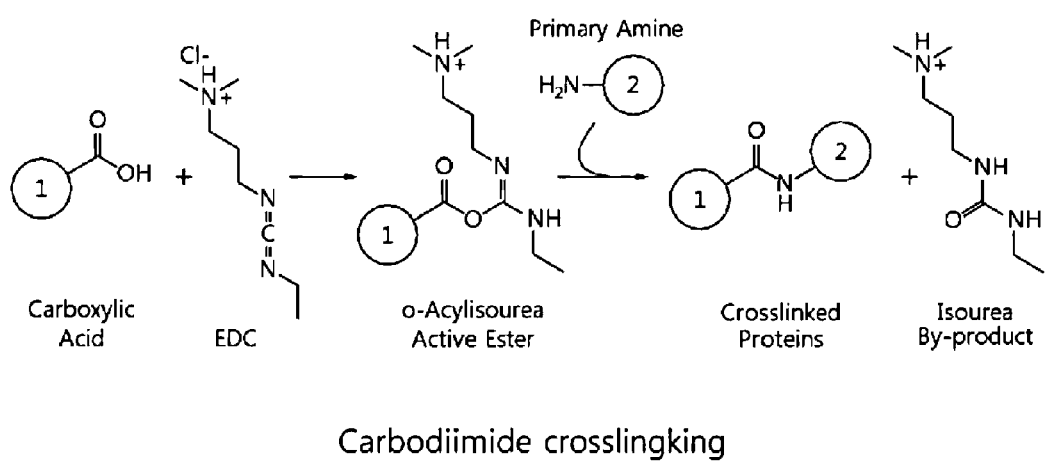
FIG. 4 illustrates an example of carbodiimide crosslinking or maleimide crosslinking according to an example embodiment.
Figure 4:
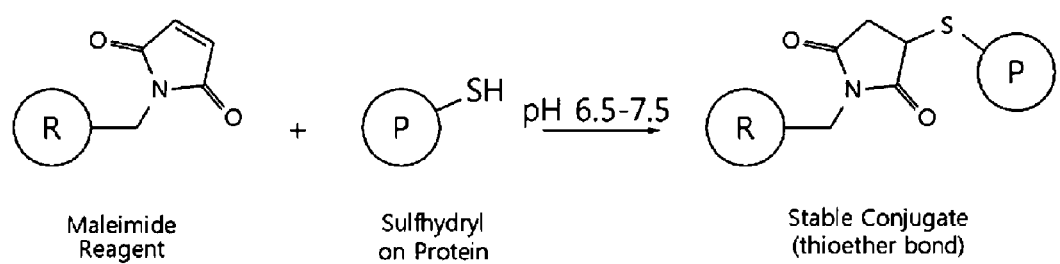

FIG. 4 illustrates an example of the above-described carbodiimide crosslinking or maleimide crosslinking.

For the carbodiimide crosslinking, at least one of 1-ethyl-3-(3-dimethylaminopropyl)carbodiimide (EDC) hydrochloride, dicyclohexylcarbodiimide (DCC), sodium cyanoborohydride (NaCNBH3), azlactone, carbonyldiimidazole (CDI), iodoacetyl, hydrazide, diaminodipropylamine (DADPA) and N-hydroxysuccinimide (NHS) esters may be used as a crosslinking agent. By adjusting a crosslinking agent, a binding characteristic between a binding mediator and a hydrogel functional layer may be controlled.

<Examples of Biochip>

(1) Biochip Including Hydrogel Functional Layer+Waveguide

In a typical light-based biochip, an optical signal applied from a light source (not shown in drawings) may be transmitted into a waveguide, and a portion of the optical signal in the waveguide may exist on a surface of the optical waveguide as a form of an evanescent electromagnetic field. Therefore, when a chemical/biological phenomenon occurs on a surface of a waveguide, an effective refractive index of a waveguide may change differently based on the types of the occurring phenomena such as chemical and biological phenomena or a degree of the phenomenon. Accordingly, optical signal transmission characteristics in the waveguide may change. A device configured to detect a change in a chemical/biological phenomenon occurring on the surface of a waveguide by evaluating transmission/diffraction/scattering/refraction/reflection/resonance characteristics of the optical signal through the waveguide may be referred to as an "optical waveguide sensor" or a "refractive index sensor."

An optical waveguide sensor or a refractive index sensor to measure a biomolecular binding relationship may have a high throughput and excellent sensitivity in comparison to other biochemical chips, may not require fluorescent labeling, and may detect the biomolecular binding relationship in real time, and thus may have significant benefits. In several approaches, a refractive index change caused by a change in a concentration of a biochemical molecule was quantified. However, an optical waveguide sensor technology for detecting multivalent bindings between the target protein and the binding mediator from monovalent bindings has not yet been implemented. A technology of accurately sensing a quantitative amount of protein with multivalent bindings distinguishably from monovalent bindings may be the basis for thrombus/immunity/cancer-related therapies and a new drug development test, and thus a technology of effectively detecting and measuring the quantitative amount of the protein multivalent bindings may be required.

Figure 5:
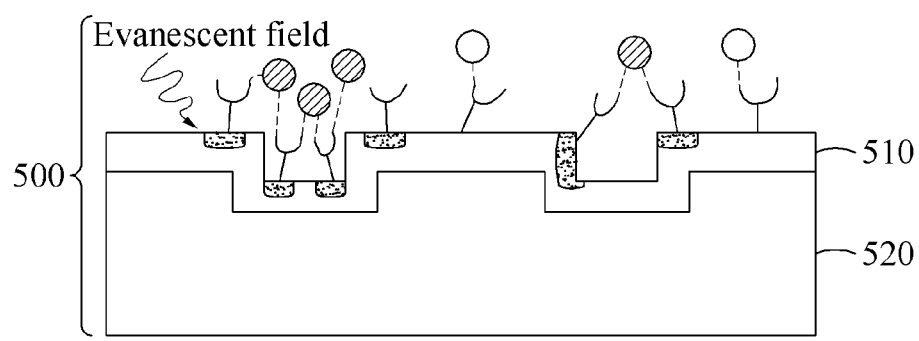
FIG. 5 illustrates an example of a biochip configured to detect a change in a refractive index of hydrogel functional layer according to an example embodiment.

FIG. 5 illustrates an example of a biochip according to an example embodiment. Referring to FIG. 5, a biochip 500 includes a hydrogel functional layer 510, and a transducer 520 that is configured to deliver a displacement signal corresponding to a change in a refractive index of the hydrogel functional layer 510 due to multivalent bindings between target protein and binding mediator to an analysis instrument.

The transducer 520 may be a waveguide. The waveguide may be, for example, one of an SPR waveguide, a ring resonator waveguide, a long-period fiber grating waveguide, a grating coupler and a grated waveguide.

The transducer 520 may produce a displacement signal, such as an optical signal or electrical signal, corresponding to a change in at least one of transmission/diffraction/scattering/refraction/reflection/resonance characteristics of an optical signal due to the change in the refractive index of the hydrogel functional layer 510. The displacement signal may be delivered to the analysis instrument, and the analysis instrument may analyze multivalent bindings between the target protein and the binding mediator in response to the displacement signal.

For example, a hydrogel functional layer may have a thickness of 10 nanometers (nm) to 1,000 nm. In an example, when a light source of about 500 nm to 1,700 nm is used, the hydrogel functional layer may have a thickness of 10 nm to 1,000 nm that is calculated using an optical waveguide simulation (e.g., a finite-difference time-domain (FDTD) method or a finite-difference method (FDM)). In this example, the hydrogel functional layer may exhibit an effective refractive index change in the thickness of 10 nm to 1,000 nm. When the thickness of the hydrogel functional layer is less than 10 nm or exceeds 1,000 nm, it may be difficult to detect multivalent bindings between the target protein and the binding mediator due to a difficulty in verifying an amount of change in the refractive index.

(2) Biochip Including Hydrogel Functional Layer+Gold Thin Film

Figure 6:
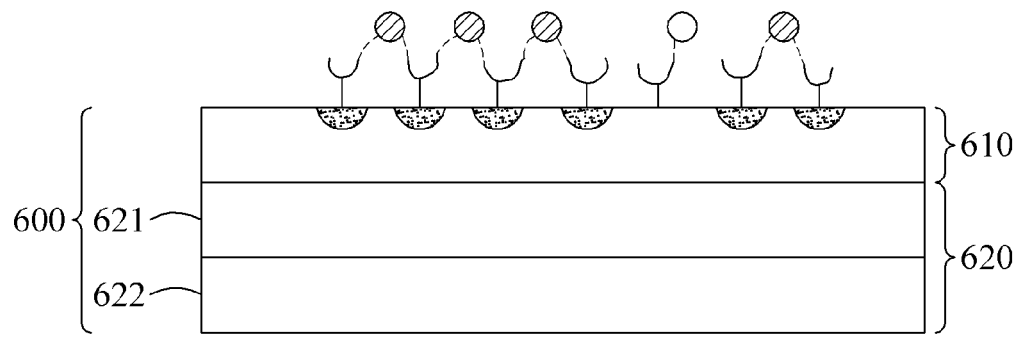
FIG. 6 illustrates another example of a biochip configured to detect a change in a refractive index of hydrogel functional layer according to an example embodiment.

FIG. 6 illustrates another example of a biochip according to an example embodiment. Referring to FIG. 6, a biochip 600 includes a hydrogel functional layer 610, and a transducer 620 that is configured to transmit a displacement signal corresponding to a change in a refractive index of the hydrogel functional layer 610 due to multivalent bindings between the target protein and the binding mediator to an analysis instrument.

The transducer 620 may comprise a layered structure of a gold thin film 621 and a glass 622. Due to a change in the refractive index in at least a portion of the hydrogel functional layer 610, an SPR may occur in the gold thin film 621. For example, a propagation angle of a signal input to the biochip 600 through an analysis instrument (not shown) may change due to the SPR occurring in the gold thin film 621, or a leakage signal may be generated on the gold thin film 621. Accordingly, a displacement signal corresponding to either the propagation angle or leakage amount change may be transmitted to the analysis instrument. The analysis instrument may analyze the displacement signal, and analyze multivalent bindings between the target protein and the binding mediator.

(3) Biochip Including Hydrogel Functional Layer+Piezoelectric Element

A biochip according to an example embodiment may include a transducer configured to deliver a displacement signal corresponding to a change in a volume of a hydrogel functional layer due to multivalent bindings between target protein and binding mediator to an analysis instrument. As described above with reference to FIG. 2, de-swelling may occur in at least a portion of the hydrogel functional layer due to the multivalent bindings between the target protein and the binding mediator, and accordingly the volume of the hydrogel functional layer may change. A piezoelectric element included in the transducer may output a displacement signal based on the above change in the volume of the hydrogel functional layer. The displacement signal may be transferred to the analysis instrument. The analysis instrument may analyze the multivalent bindings between the target protein and the binding mediator based on the change in the volume.

(4) Multi-Channel Biochip

Figure 7:
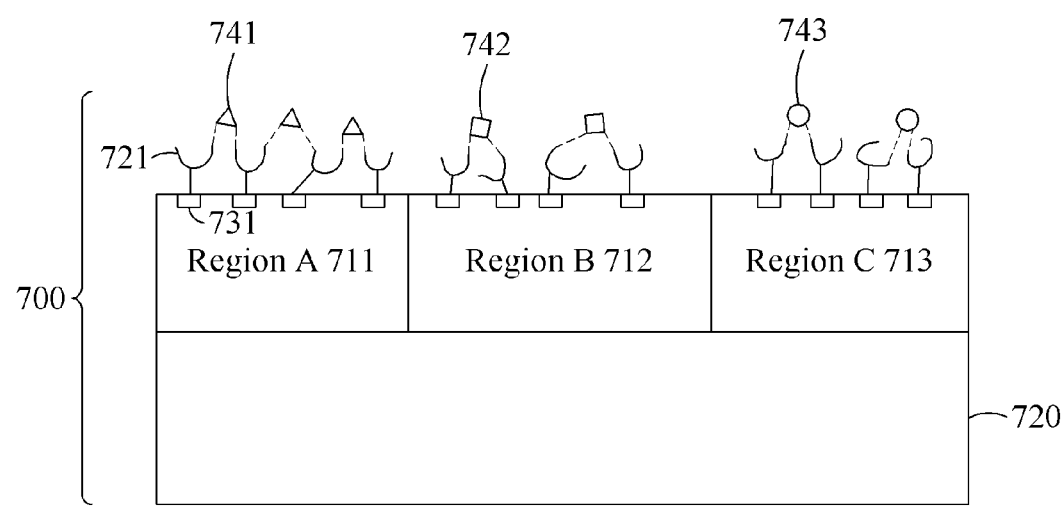
FIG. 7 illustrates an example of a biochip employing multi-channel hydrogel functional layer according to an example embodiment.

FIG. 7 illustrates still another example of a biochip according to an example embodiment.

A biochip 700 according to an example embodiment may include at least two segmented regions of hydrogel functional layers. In an example, the segmented hydrogel functional layers of 711, 712 and 713 are physically divided to detect and compare multivalent bindings between different pairs of target proteins and binding mediators.

In another example, the divided hydrogel functional layers of 711, 712 and 713 may be formed using different hydrogel composition.

Multivalent bindings may be taken place between target protein 741 and binding mediator 721 formed in a region A 711 of the hydrogel functional layer, and accordingly a de-swelling region 731 may be formed in the region A 711.

Multivalent bindings may be taken place between target protein 742 and binding mediator formed in a region B 712 of the hydrogel functional layer, and accordingly a de-swelling region may be formed in the region B 712.

Multivalent bindings may be taken place between target protein 743 and binding mediator formed in a region C 713 of the hydrogel functional layer, and accordingly a de-swelling region may be formed in the region C 713.

The transducer 720 may deliver a displacement signal corresponding to each of the regions A 711 through C 713 to an analysis instrument, based on a change in physical properties of each of the regions A 711 through C 713 due to the de-swelling regions in the regions A through C.

The displacement signal may be analyzed by the analysis instrument, and multivalent bindings between the target proteins and the binding mediators for each region corresponding to a change in physical properties of each region may be analyzed.

<Method of Manufacturing Biochip>

Figure 8:
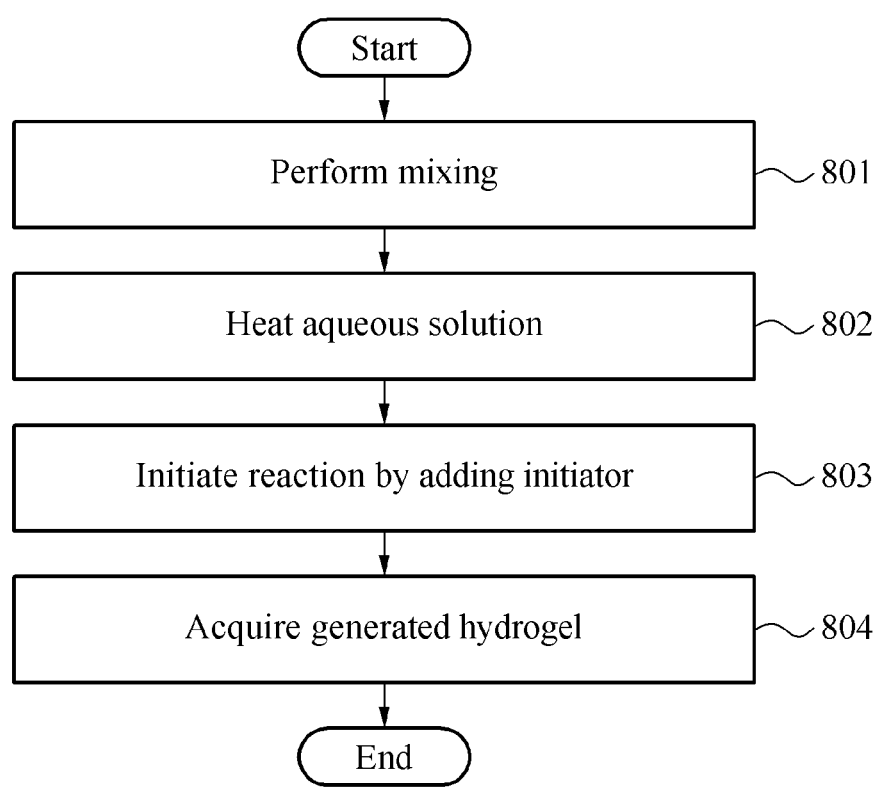
FIG. 8 illustrates an example of a synthesis method of hydrogel used to form hydrogel functional layer according to an example embodiment.

(1) Method of Manufacturing Biochip Using Hydrogel in Form of Nanoparticle:

FIG. 8 illustrates a hydrogel synthesis method to form a hydrogel functional layer of a biochip according to an example embodiment.

A hydrogel used to form the hydrogel functional layer of the biochip may be prepared by operation 801 of mixing 55 to 98% of a main monomer, 2 to 40% of comonomers and 0.1 to 5% of a crosslinking agent so that a sum of the main monomer and the comonomers is 100%; operation 802 of heating an aqueous solution containing the main monomer and the comonomers; operation 803 of initiating a reaction by adding an initiator; and operation 804 of acquiring an aqueous hydrogel solution generated by the reaction.

In operation 801, the main monomer and the comonomers are polymerized by the crosslinking agent, to form the hydrogel. Monomers capable of forming a hydrogel functional layer sensitive to heat or pH may desirably be used.

For example, the main monomer may be one of N-isopropylacrylamide, poly(N-acryloylglycinamide), hydroxypropylcellulose, poly(vinylcaprolactame) and polyvinyl methyl ether. The comonomer may be one of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

The hydrogel may include 55 to 98% of the main monomer, 2 to 40% of the comonomer and 0.1 to 5% of the crosslinking agent.

When the amount of the main monomer is less than 55%, a reactivity may decrease. When the amount of the main monomer exceeds 98%, a capability to detect a dimerization of a protein may decrease.

When the amount of the comonomers is less than 2% or exceeds 40%, a capability to detect a dimerization of a protein may decrease. When the amount of the crosslinking agent is less than 0.1%, it may be difficult to form the hydrogel functional layer. When the amount of the crosslinking agent exceeds 5%, a capability (e.g., a resolution capability) to detect a dimerization of a protein may decrease.

For example, the main monomer may be N-isopropylacrylamide (a temperature-sensitive hydrogel), and the comonomer may be acrylic acid (that is, a pH-sensitive hydrogel). In this example, a crosslinking agent may be N, N'-methylene-bis-acrylamide (BIS).

The hydrogel may include at least one of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

For example, the hydrogel may include 55 to 98% of N-isopropylacrylamide, 2 to 40% of acrylic acid, and 0.1 to 5% of a BIS crosslinking agent. In particular, when acrylic acid is used as comonomers, at least 2% of the acrylic acid may desirably be included in materials that form the hydrogel functional layer.

The aqueous solution containing the main monomer and the comonomers is heated in operation 802.

The reaction is initiated by adding the initiator to the heated aqueous solution in operation 803. The initiator may include, for example, ammonium persulfate (APS).

The aqueous hydrogel solution generated by the reaction is acquired in operation 804. Operation 804 may include maintaining an oxygen-free environment while heating the aqueous solution. For example, when an oxygen-free environment is maintained, a uniformity of a size of the hydrogel acquired in operation 804 may increase.

Also, operation 804 may include dialyzing and purifying an unreacted monomer.

The above-described hydrogel may control a sensitivity to multivalent bindings between a target protein and a binding mediator by adjusting a ratio between components. The above composition of the hydrogel and the method of preparing the hydrogel are not limited to examples described in the present disclosure. For example, when a specific gravity of acrylic acid increases and a specific gravity of a BIS crosslinking agent decreases, a reactivity (e.g., a degree of de-swelling) of the hydrogel functional layer to the multivalent binding may increase.

Based on the hydrogel synthesis method of FIG. 8, a hydrogel in a form of nanoparticles may be synthesized.

Figure 9:
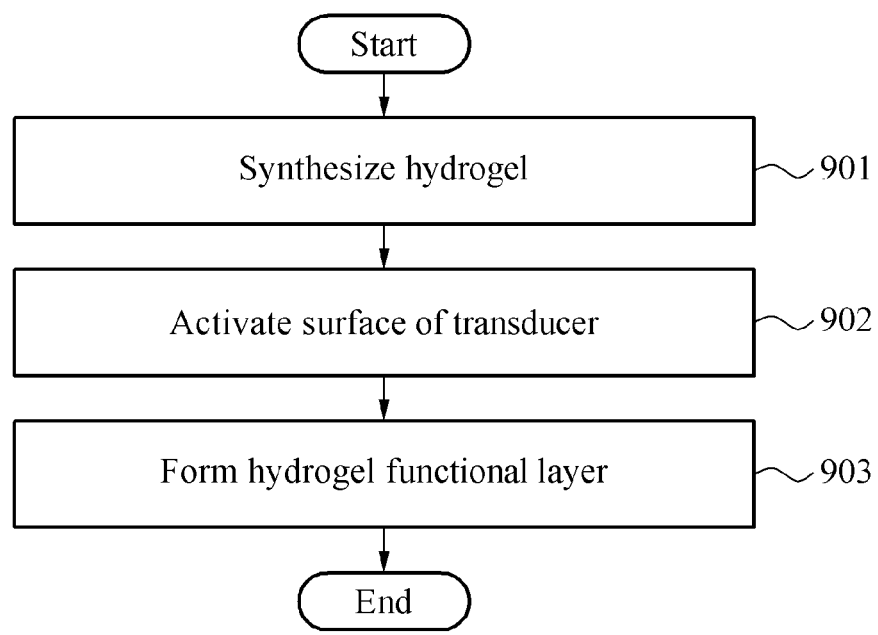
FIG. 9 illustrates an example of a method of manufacturing a biochip to form hydrogel functional layer using hydrogel synthesized by the synthesis method of FIG. 8.

FIG. 9 illustrates a method of manufacturing a biochip by forming the hydrogel synthesized by the hydrogel synthesis method of FIG. 8 on a transducer.

The method of manufacturing a biochip includes operation 901 of synthesizing a hydrogel in a form of nanoparticles; operation 902 of activating a surface of the transducer with at least one of positive charge, negative charge, epoxy and mercapto; and operation 903 of forming a hydrogel functional layer by applying the hydrogel to the surface of the transducer.

The hydrogel in the form of nanoparticles may be synthesized based on the hydrogel synthesis method of FIG. 8 in operation 901.

The surface of the transducer is activated with at least one of the positive charge, the negative charge, the epoxy and the mercapto in operation 902.

Operation 902 of activating the surface of the transducer with at least one of the positive charge, the negative charge, the epoxy and the mercapto may be performed through a reaction on an aqueous solution using at least one of aminosilane, epoxysilane and mercaptosilane.

The aminosilane may be one of (3-aminopropyl)-triethoxysilane, bis[(3-triethoxysilyl)propyl]amine, (3-aminopropyl)-trimethoxysilane, bis[(3-trimethoxysilyl)propyl]amine, (3-aminopropyl)-methyl-diethoxysilane, (3-aminopropyl)-dimethyl-ethoxysilane, (3-aminopropyl)-diethoxy-methylsilane, aminoethyl-aminopropyl-trimethoxysilane, aminoethyl-aminopropyl-methyl-dimethoxysilane, diethylenetriaminopropyl-methyl-dimethoxysilane, piperazinylpropyl-methyl-dimethoxysilane, (N-phenylamino)methyl-trimethoxysilane, (N-phenylamino)methyl-triethoxysilane, (N-phenylamino)propyl-trimethoxysilane, dimethyl-aminoethyl-triethoxysilane, diethyl-aminomethyl-methyl-diethoxysilane and diethyl-aminopropyl-trimethoxysilane.

The epoxysilane may be one of 3-glycidoxypropyl-trimethoxysilane, 3-glycidoxypropyl-triethoxysilane, 3-glycidoxypropyl-methyl-diethoxysilane, 3-glycidoxypropyl-methyl-dimethoxysilane, 2-(3,4-epoxycyclohexyl)ethyl-trimethoxysilane and 2-(3,4-epoxycyclohexyl)ethyl-triethoxysilane.

The mercaptosilane may be one of (3-mercaptopropyl)-trimethoxysilane (MPTMS) having a thiol group, (3-mercaptopropyl)-triethoxysilane and (3-mercaptopropyl)-methyl-dimethoxysilane (MPDMS).

The hydrogel functional layer is formed by applying the hydrogel to the surface of the transducer in operation 903.

To uniformly apply the hydrogel functional layer to the surface of the transducer, the surface of the transducer may have a positive charge (+) and the hydrogel functional layer may be activated with a negative charge (−) in advance.

For example, when a hydrogel functional layer is formed in a form of nanoparticles, an aqueous free-radical precipitation polymerization method may be used.

In an example, a surface of the hydrogel functional layer may be modified by forming a binding mediator that may be at least one of a ligand, a receptor, DNA and RNA.

In another example, the surface of the hydrogel functional layer may be modified by using at least one of nanoparticles and protein as a linking conjunction to form a binding mediator that may be at least one of a ligand, a receptor, DNA and RNA.

The binding mediator may be linked to the hydrogel functional layer by at least one of carbodiimide crosslinking, Schiff base crosslinking, azlactone crosslinking, carbonyldiimidazole (CDI) crosslinking, iodoacetyl crosslinking, hydrazide crosslinking, Mannich crosslinking and maleimide crosslinking. A carboxylic acid functional group (COOH) present on the surface of the hydrogel functional layer, and a $NH_2^+$ group present on a protein may be used to form the binding mediator on the surface of the hydrogel functional layer.

For the carbodiimide crosslinking, at least one of 1-ethyl-3-(3-dimethylaminopropyl)carbodiimide (EDC) hydrochloride, dicyclohexylcarbodiimide (DCC), sodium cyanoborohydride (NaCNBH3), azlactone, carbonyldiimidazole (CDI), iodoacetyl, hydrazide, diaminodipropylamine (DADPA) and N-hydroxysuccinimide (NHS) esters may be used as a crosslinking agent. By adjusting a crosslinking agent, a binding characteristic between a binding mediator and a hydrogel functional layer may be controlled.

For example, the hydrogel functional layer may be modified by a method of forming a binding mediator on the surface of the hydrogel functional layer using at least one crosslinking agent among 1-ethyl-3-(3-dimethylaminopropyl)carbodiimide (EDC) hydrochloride, dicyclohexylcarbodiimide (DCC), sodium cyanoborohydride (NaCNBH3), azlactone, carbonyldiimidazole (CDI), iodoacetyl, hydrazide, diaminodipropylamine (DADPA) and N-hydroxysuccinimide (NHS) esters. In this example, a binding characteristic between the binding mediator and the hydrogel functional layer may be controlled by adjusting the crosslinking agent.

(2) Method of Manufacturing Biochip Using Hydrogel in Form of Bulk Gel:

In a biochip according to an example embodiment, a hydrogel functional layer may be formed in a form of a bulk gel.

Figure 10:
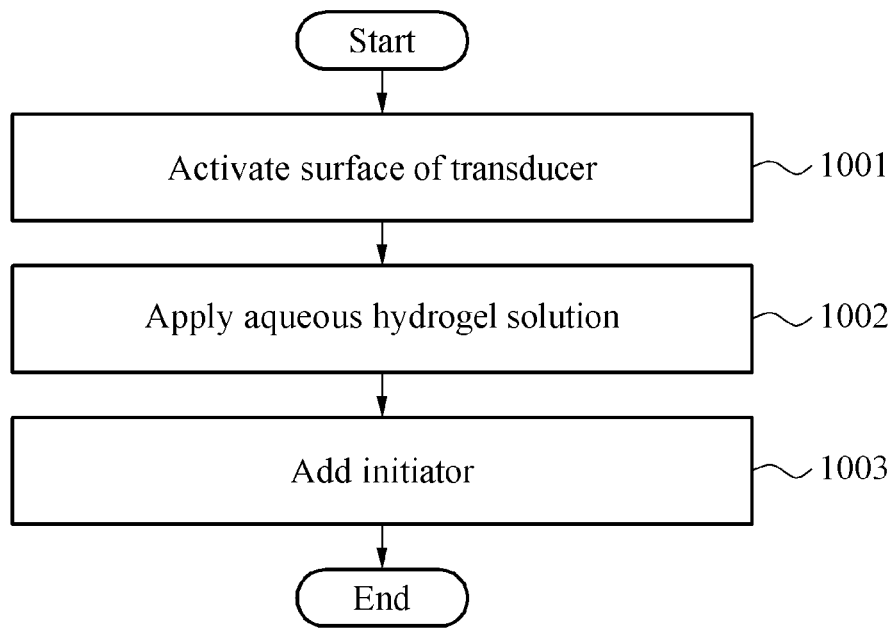
FIG. 10 illustrates an example of a method of manufacturing a biochip using a hydrogel in a form of a bulk gel according to an example embodiment.

FIG. 10 illustrates a method of manufacturing a biochip using a hydrogel in a form of a bulk gel according to an example embodiment. Here, a method of initiating a polymerization reaction by filling a surface of a transducer with a reactant (in a liquid phase) may be used.

The method of manufacturing a biochip using a hydrogel in a form of a bulk gel includes operation 1001 of activating a surface of a transducer with at least one of positive charge, negative charge, epoxy and mercapto using an aqueous hydrogel solution in a form of a bulk gel; operation 1002 of applying the aqueous hydrogel solution to the surface of the transducer; and operation 1003 of forming a hydrogel functional layer in a form of a bulk gel by adding an initiator to the aqueous hydrogel solution.

The aqueous hydrogel solution may include 55 to 98% of a main monomer, 2 to 40% of comonomers and 0.1 to 5% of a crosslinking agent.

For example, the main monomer may be one of N-isopropylacrylamide, poly(N-acryloylglycinamide), hydroxypropylcellulose, poly(vinylcaprolactame) and polyvinyl methyl ether. The comonomer may be at least one of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

The aqueous hydrogel solution may include at least one of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

The surface of the transducer is activated with at least one of the positive charge, the negative charge, the epoxy and the mercapto in operation 1001. Operation 1001 is the same as operation 902 described above, and accordingly further description thereof is omitted here.

The aqueous hydrogel solution is applied to the surface of the transducer in operation 1002. When the aqueous hydrogel solution is applied to the surface of the transducer, a thickness of the hydrogel functional layer may be adjusted by changing a level of hydrogel solution.

The hydrogel functional layer in a form of a bulk gel may be formed by adding the initiator to the aqueous hydrogel solution in operation 1003. A scheme of adding the initiator is the same as that described in operation 1003, and accordingly further description thereof is omitted here.

In an example, the method may further include modifying a surface of the hydrogel functional layer by forming a binding mediator on the surface of the hydrogel functional layer.

In another example, the method may further include modifying a surface of the hydrogel functional layer by using at least one of nanoparticles and protein as a coupling moiety to form a binding mediator on the surface of the hydrogel functional layer.

As described above, the binding mediator may include, for example, at least one of a receptor, a ligand, DNA and RNA. For example, the binding mediator may be formed by mixing at least two of the receptor, the ligand, the DNA and the RNA.

The modifying of the surface of the hydrogel functional layer has been described above, and accordingly further description thereof is omitted here.

<Experimental Example of Biochip>

A "biochip including a gold thin film having a surface modified with PEG/COOH" that is generally used, and a "biochip including a hydrogel functional layer formed on a surface of a gold thin film" that is manufactured by a special technology, were used as biochips to detect a multivalent binding using a commercially available SPR sensors by the applicant. The above two biochips were each mounted in Reichert®'s SPR sensors that are analysis instruments, and experiments were conducted. The above description of FIG. 6 is also applicable to the biochip including the hydrogel functional layer formed on the surface of the gold thin film, and accordingly is not repeated here.

In the "biochip including the hydrogel functional layer formed on the surface of the gold thin film," a surface was modified using cystamine dihydrochloride to form the hydrogel functional layer.

Binding mediators were formed on the "biochip including the gold thin film having the surface modified with PEG/COOH" and the "biochip including the hydrogel functional layer formed on the surface of the gold thin film." Here, the two types of binding mediators were specially designed by the applicants so that either a monovalent or a multivalent binding is dominantly generated when a binding state is formed by the insertion of a target protein.

Accordingly, when a target protein is introduced to the two types of the biochips, respectively, the following four cases may occur considering both the biochip types and protein binding states:

1) monovalent bindings of protein to the "biochip including the gold thin film having the surface modified with PEG/COOH";

2) monovalent bindings of protein to the "biochip including the hydrogel functional layer formed on the surface of the gold thin film";

3) multivalent bindings of protein to the "biochip including the gold thin film having the surface modified with PEG/COOH"; and 4) multivalent bindings of protein to the "biochip including the hydrogel functional layer formed on the surface of the gold thin film."

Target protein with the same concentration was introduced throughout the experiment. Binding reactions between the target protein and two types of binding mediators (i.e.; monovalent binding mediators and multivalent binding mediators) were evaluated in each biochips (i.e.; PEG/COOH modified biochip and hydrogel functional layer biochips). The results were measured using the SPR sensor after a predetermined period of time.

Figure 11A:
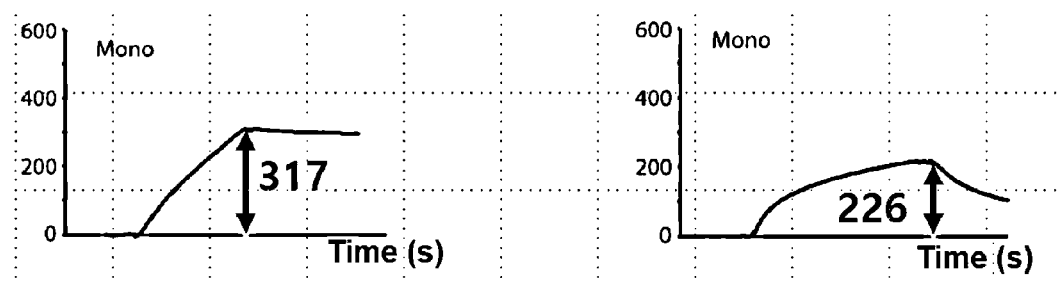
FIGS. 11A and 11B illustrate performance experimental results of biochips according to an example embodiment.
Figure 11B:
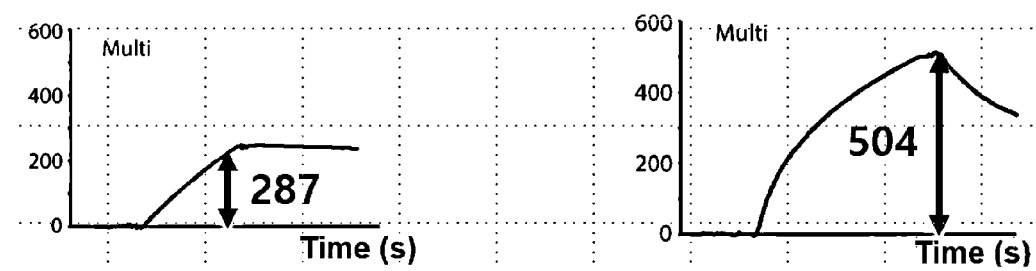

FIGS. 11A and 11B illustrate experimental results of biochips according to an example embodiment.

A left graph of FIG. 11A illustrates a response magnitude 317 of the SPR sensor in case 1). A right graph of FIG. 11A illustrates a response magnitude 226 of the SPR sensor in case 2).

A left graph of FIG. 11B illustrates a response magnitude 287 of the SPR sensor in case 3). A right graph of FIG. 11B illustrates a response magnitude 504 of the SPR sensor in case 4).

When the "biochip including the gold thin film having the surface modified with PEG/COOH" is used (the left hand side plots of FIGS. 11A and 11B), a meaningful magnitude difference is not observed between the monovalent and multivalent binding cases. Therefore, the "biochip including the gold thin film having the surface modified with PEG/COOH" might not be used to measure the multivalent binding nor distinguish monovalent and multivalent binding states. Instead, the response magnitude of the monovalent bindings is higher than that of the multivalent bindings that may affect significantly as noise to measure multivalent bindings.

When the "biochip including the hydrogel functional layer formed on the surface of the gold thin film" is used (the right hand side plots of FIGS. 11A and 11B), a significant magnitude difference between the monovalent and multivalent bindings is observed. More than 2-folds of the response magnitude is measured as shown in the figures. This is due to the fact that the physical properties of the hydrogel functional layer changes significantly under the multivalent binding state whereas it does not change under the monovalent binding state. The exact amount of the multivalent bindings may be acquired by subtracting a response magnitude obtained using a PEG/COOH layer biochip from a response magnitude obtained using a biochip including a hydrogel functional layer. Furthermore, the amount of multivalent bindings by unknown target proteins may be easily evaluated that realizes the identification of the target protein.

While example embodiments have been shown and described with reference to the accompanying drawings, it will be apparent to those skilled in the art that various modifications and variations can be made from the foregoing descriptions. For example, adequate effects may be achieved even if the foregoing processes and methods are carried out in different order than described above, and/or the aforementioned components are combined or coupled in different forms and modes than as described above or be substituted or switched with other components or equivalents.

Therefore, other implementations, alternative example embodiments and equivalents to the claimed subject matter are construed as being within the appended claims.

The invention claimed is:

1. A biochip comprising:
   a hydrogel functional layer on which a binding mediator is formed and of which physical properties are changed by a reaction between target protein to be introduced and the binding mediator; and
   a transducer configured to deliver a displacement signal corresponding to a change in the physical properties of the hydrogel functional layer to an analysis instrument,
   wherein the hydrogel functional layer is attached to a surface of the transducer and the hydrogel functional layer consists of 55 to 98% of a main monomer, 2 to 40% of comonomers and 0.1 to 5% of a crosslinking agent so that a sum of the main monomer, the comonomers, and the crosslinking agent is 100%;
   wherein the surface of the transducer is activated with at least one of positive charge, negative charge, epoxy and mercapto; and
   wherein the reaction is multivalent bindings between the target protein and the binding mediator, and de-swelling occurs in at least a portion of the hydrogel functional layer by the multivalent bindings.

2. The biochip of claim 1, wherein
   the physical properties comprise a refractive index of at least a portion of the hydrogel functional layer,
   the transducer comprises a waveguide, and the displacement signal is an output signal of the waveguide.

3. The biochip of claim 1, wherein
the physical properties comprise a refractive index of at least a portion of the hydrogel functional layer,
the transducer comprises a gold thin film, and
the displacement signal is a signal corresponding to a surface plasmon resonance (SPR) occurring in the gold thin film.

4. The biochip of claim 1, wherein
the main monomer is selected from the group consisting of N-isopropylacrylamide, poly(N-acryloylglycinamide), hydroxypropylcellulose, poly(vinylcaprolactame) and polyvinyl methyl ether, and
the comonomers are selected from the group consisting of allylamine (AA), dimethylaminoethyl methacrylate (DMAEMA), dimethylaminoethyl acrylate (DMAEA), acrylic acid (AAc), polyethylene glycol (PEG) and methacrylic acid (MAAc).

5. The biochip of claim 1, wherein the hydrogel functional layer comprises at least one selected from the group consisting of poly(N-isopropylacrylamide-co-allylamine) (poly(NIPAM-co-AA)), poly(N-isopropylacrylamide-co-2-(dimethylamino)ethyl methacrylate) (poly(NIPAM-co-DMAEMA)), poly(N-isopropylacrylamide-co-2-(dimethylamino)ethyl acrylate) (poly(NIPAM-co-DMAEA)), poly(N-isopropylacrylamide-co-acrylic acid) (poly(NIPAM-co-AAc)), poly(N-isopropylacrylamide-co-polyethylene glycol-acrylic acid) (poly(NIPAM-co-PEG-AAc)), [poly(N-isopropylacrylamide-co-methacrylic acid) (poly(NIPAM-co-MAAc)), N-isopropylacrylamide, poly(N-acryloylglycinamide), hydroxypropylcellulose, poly(vinylcaprolactame) and polyvinyl methyl ether.

6. The biochip of claim 1, wherein
the binding mediator is at least one of a ligand, a receptor, deoxyribonucleic acid (DNA) and ribonucleic acid (RNA), and
a surface of the hydrogel functional layer is modified by forming the binding mediator.

7. The biochip of claim 1, wherein
the binding mediator is at least one of a ligand, a receptor, DNA and RNA, and
a surface of the hydrogel functional layer is modified using at least one of nanoparticles and protein as a coupling moiety to form the binding mediator.

8. The biochip of claim 1, wherein a region of the hydrogel functional layer is divided into at least two regions for reaction with the target protein.

* * * * *